(12) United States Patent
Romaine

(10) Patent No.: US 11,040,003 B2
(45) Date of Patent: Jun. 22, 2021

(54) AQUEOUS PERFUMES

(71) Applicant: CHANEL INC, New York, NY (US)

(72) Inventor: Carolyn Romaine, Piscataway, NJ (US)

(73) Assignee: CHANEL INC, New York, NY (US)

( * ) Notice: Subject to any disclaimer, the term of this patent is extended or adjusted under 35 U.S.C. 154(b) by 0 days.

(21) Appl. No.: 16/722,395

(22) Filed: Dec. 20, 2019

(65) Prior Publication Data

US 2020/0197290 A1    Jun. 25, 2020

(30) Foreign Application Priority Data

Dec. 20, 2018 (EP) .................................. 18214914

(51) Int. Cl.
| | | |
|---|---|---|
| *A61K 8/00* | (2006.01) | |
| *A61K 8/18* | (2006.01) | |
| *A61Q 13/00* | (2006.01) | |
| *A61K 8/86* | (2006.01) | |

(52) U.S. Cl.
CPC ............ *A61K 8/86* (2013.01); *A61K 2800/30* (2013.01); *A61K 2800/43* (2013.01); *A61K 2800/524* (2013.01); *A61K 2800/77* (2013.01)

(58) Field of Classification Search
CPC .... A61K 8/86; A61K 8/345; A61K 2800/524; A61K 2800/77; A61K 2800/30; A61K 2800/43; A61Q 13/00

USPC ........................................................ 512/2, 1
See application file for complete search history.

(56) References Cited

U.S. PATENT DOCUMENTS

| | | | |
|---|---|---|---|
| 2004/0014879 A1* | 1/2004 | Denzer ................... | A61K 8/39 524/588 |
| 2004/0214740 A1 | 10/2004 | Barberan et al. | |
| 2013/0101531 A1 | 4/2013 | Shick et al. | |
| 2015/0118328 A1* | 4/2015 | Castan Barberan ..... | A61K 8/39 424/725 |

OTHER PUBLICATIONS

International Search Report and Written Opinion dated Jun. 11, 2020, in corresponding International application No. PCT/IB 20/51346; 13 pages.

* cited by examiner

*Primary Examiner* — Jessica Whiteley
(74) *Attorney, Agent, or Firm* — Maier & Maier, PLLC

(57) ABSTRACT

Leave-on ethanol-free water-based perfumed compositions which are stable during storage, in particular remain clear during storage, and which are non-irritating to the skin. An ethanol-free perfumed composition including water, a perfume and an ester, wherein the ester includes an ethoxylated glyceride derived from carboxylic acids having 6 to 22 carbon atoms moiety.

16 Claims, No Drawings

AQUEOUS PERFUMES

FIELD

The present invention relates to ethanol-free perfumed compositions suitable for leave-on cosmetics, said compositions being clear, transparent and stable during storage. The invention is also directed to ethanol-free perfumed products obtainable by dilution in water of ethanol-free perfume preparations.

BACKGROUND

Historically, perfumes have been prepared by dissolving fragrance oils in volatile alcohols, primarily ethanol, or in a mixture of ethanol and water. The industrialization of surfactants and the advances in colloid science have made possible the solubilization of fragrances in water by means of emulsification with surfactants. When an emulsion has a particle size of about 140 nm or less it is referred to as a microemulsion. The small size of these microemulsions containing fragrance oils results in perfume products that are clear or almost clear, and are not very different in appearance to conventional ethanol-based perfumes. Microemulsions contain physical structures which can be described as swollen micelles, inversed micelles or continuous bi-layers. None of these structures are present in conventional ethanol-based perfume products.

The key benefit of water-based perfumes is a reduction in VOC's (Volatile Organic Compounds). Another benefit is the immediate perception of the intrinsic nature of the fragrance oils due to the absence of ethanol or ethanol-like alcohols. However, microemulsion water-based products tend to be foamy, sticky or even irritating to the skin due to presence of the surfactants required to solubilize the fragrance.

These drawbacks are magnified as the surfactant or the perfume content increases. This content depends on the intrinsic efficiency of the selected surfactant system, the ease or difficulty of solubilization of the fragrance oil itself, and the total content of the fragrance oil in the final perfume product. In any case, T. J. Lin mentioned in Surfactants in Cosmetics, Surfactants Sci. Ser. Vol. 16, (1985), 29-52, that the practical preparation of these microemulsion products will need a ratio of surfactant solubilizer system to fragrance oil much greater than 1/1. There is therefore a need to make the microemulsions with low concentrations of skin compatible surfactants.

U.S. Pat. No. 5,374,614 discloses low VOC microemulsions for perfumery applications with reduced surfactant content. The surfactant system consists of a non-ionic fraction and an anionic fraction, which are also representative of other disclosures in the art, such as in U.S. Pat. No. 7,655,613.

The non-ionic fraction in these documents is based on ethoxylated surfactants that are known for their excellent fragrance solubilization properties. Both patents disclose a long list of ethoxylated compounds. However, ethoxylated surfactants with molecular weights in the 400 to 1200 range and based on fatty acids, fatty alcohols, and even the alkyl phenol as disclosed in U.S. Pat. No. 5,374,614 and no longer used in consumer products, are known to disrupt the lipids of the stratum corneum. While acceptable for usage in many consumer and industrial products, where they may have functions in addition to fragrance solubilization, these surfactants are not very suited for perfume products for application to the skin or hair. Ethoxylated non-ionic surfactants with high molecular weight, such as the ethoxylated castor oil materials disclosed in U.S. Pat. No. 8,461,099, are very suited for perfumes for personal use.

The anionic surfactants disclosed in these patents are also known for their use in many personal cleansing products, household products, laundry products and detergent products in general. They are known to negatively interact with the corneocites of the skin to cause irritation, especially when left deposited on the skin, as it is the case of perfumery products intended for personal use.

There remains therefore a need for ethanol-free water-based perfumed compositions that remain transparent and stable over time while being non-irritant to the skin.

The present invention provides an unexpected and advantageous solution to all these requirements with the incorporation of news specific esters that totally replace the ethanol or the anionic materials described as indispensable in the prior art. An object of the present invention is therefore to provide new leave-on ethanol-free water-based perfumed compositions which are stable to storage, in particular remain clear and which are non-irritant to the skin.

SUMMARY

The present invention relates to an ethanol-free perfumed composition comprising water, a perfume and an ester, wherein the ester comprises an ethoxylated glyceride derived from carboxylic acids having 6 to 22 carbon atoms moiety.

The present invention is also directed to a Method for the preparation of said ethanol-free perfumed composition, comprising the following steps:
a. preparing a solution of water and the ester under stirring, and mixing until a clear and uniform solution is obtained,
b. adding the perfume to the solution and mixing until a clear and uniform solution is obtained.

The present invention is also directed to the use of said perfumed composition for the preparation of a fine perfume composition, or a cosmetic composition or a personal cleansing composition.

This invention also pertains to the use of an ester comprises an ethoxylated glyceride derived from carboxylic acid having 6 to 22 carbon atoms moiety to improve solubility of a perfume in water and/or confer transparency to perfumed composition comprising water and perfume.

It is of the merit of the inventors to have discovered that the combination of specific esters, perfume and water made it possible to provide clear, transparent and storage stable ethanol-free perfumed compositions that are perfectly non-irritant to the skin.

In particular, within the meaning of the invention, the pH of the compositions remains stable over time (at least up to 3 weeks, and preferably up to 12 weeks) during storage at 5° C. or 45° C. By stable, it is understood that the Variation of pH under the different storage conditions tested does not exceeds 1 pH unit.

DETAILED DESCRIPTION

Ethanol-Free Composition

Ethanol-free perfumed composition, in the context of the invention, are compositions which comprises less than 5% by weight of ethanol, preferably less than 4% by weight, more preferably less than 3% by weight, even more preferably less than 2% by weigh, and further more preferably less than 1% by weight and in a more preferred embodiment, the composition is free from ethanol.

Water

The perfumed compositions of the present invention comprise at least 50% by weight water. In one embodiment, the compositions comprise from 5% to 75% by weight water. In a further embodiment, the compositions comprise from 10% to 50% by weight water, preferably from 15% to 30% by weight water.

Perfumes

As mentioned above, the alcohol-free composition of the present invention comprises at least one perfume.

In the context of this specification the term «perfume» is understood as referring to one or a mixture of olfactively active materials currently used in perfumery, providing a pleasant smell. Mixture of perfumes can be referred to as «perfumed composition». The perfume can be of natural or synthetic origin. In a general manner perfumes are hydrophobic compound belong to chemical classes as varied as terpenes hydrocarbons, acetates, alcohol, aldehydes, ketones, esters, ethers, nitriles, nitrogenous or sulphurous heterocyclic compounds and essential oils of natural or synthetic origin. A more detailed description is not warranted here since skilled persons are familiar with the ingredients and able to select them according to the nature of the product to be perfumed and the desired olfactory effect.

Water solubility of the fragrances is inversely correlated with the theoretical octanol/water partition coefficient usually expressed in the logarithm as "log P octanol/water" or "log Pow". Low log Pow values indicate more water soluble molecules while higher log Pow values are indicating a more hydrophobic compound. However, the log Pow characterizes fragrances in a chemical environment free of surfactants. When surfactants are present, the log Pow may only provide a partial description of the fragrance intrinsic solubility that is now governed by the incorporation of the fragrance ingredients into the various sites of the surfactant micelles.

In one embodiment, the composition comprised 1% to 40%, preferentially between 2% to 25% by weight, relative to the total weight of the composition of perfume.

Polar Emollient Ester

The invention's perfumed composition also comprises a polar emollient ester. Polar emollient ester is defined, within the meaning of the invention, as amphiphilic polymers. The term amphiphilic defines a molecule comprising a water soluble moiety and an oil soluble moiety. Indeed, this class has strong affinity, and can possibly form chemical bonds, to polar materials so to perfume.

Accordingly, the present invention relates to an ethanol-free perfumed composition, the ester comprises an ethoxylated glyceride derived from carboxylic acids having 6 to 22 carbon atoms moiety.

In a preferred embodiment, the ethoxylated glyceride derived from carboxylic acids having 6 to 22 carbon atoms includes compounds of the following formula (I):

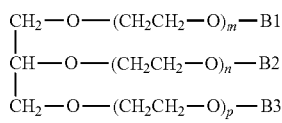

Formula (I)

wherein each of m, n, and l independently represent a number from 0 to 40,
the sum of m, n and l being in the range of 8 to 200, preferably 9 to 30; more preferably 15 to 25 and
B1, B2, and B3 independently represent H or an acyl residue having 6 to 22 carbon atoms, with the proviso that at least one of B1, B2 and B3 is an acyl residue having 6 to 22 carbon atoms.

In particular, the ethoxylated glyceride is desirably used as a mixture compounds of the above formula (I) comprising:

(i) compounds of formula (I), wherein each of B1, B2 and B3 independently represent an acyl group having 6 to 22 carbon atoms;
(ii) compounds of formula (I), wherein two of B1, B2 and B3 independently represent an acyl group having 6 to 22 carbon atoms, the remainder representing H;
(iii) compounds of formula (I), wherein one of B1, B2 and B3 represents an acyl group having 6 to 22 carbon atoms; the remainder representing H;
(iv) compounds of formula (I), wherein each of B1, B2 and B3 represent H; the weight ratio of the compounds (i)/(ii)/(iii) being 46 to 90/9 to 35/1 to 15.

These compounds are preferably prepared by a reaction between triglyceride and glyceride and ethylene oxide.

The acyl group having 6 to 22 carbon atoms, desirably 12 to 18 carbon atoms, is preferably derived from a natural fat or oil or a synthetic glyceride. Preferred fats and oils include vegetable palm kernel oil, sunflower oil, rapeseed oil, castor oil, olive oil, soybean oil; and animal fat such as tallow, bone oil, fish oil, hardened oils and semihardened oils thereof; and mixture thereof. Particularly preferred are acyl groups derived from coconut oil, palm oil and tallow such as beef tallow.

A preferred ethoxylated glyceride is the glycereth-17 cocoate, marketed under the trade name LEVENOL C-201B by Kao S. A. This is a mixture of compounds of the above formula (I) wherein the sum of m, n and l is 17 and either one or two groups of B1 and B2 are acyl groups derived from coconut oil or wherein the ester comprises glycereth-20 cocoate, which is a mixture of compounds formula (I) wherein the sum of m, n, and l is 20 and either one or two groups of B1 and B2 are acyl groups derived from coconut oil.

Another preferred ethoxylated glyceride is the glycereth-20 cocoate. This is a mixture of compounds of the above formula (I) wherein the sum m, n and p is 20 and either one or two groups of B1 and B2 are acyl groups derived from coconut oil.

In one embodiment, the weight ratio of the perfume to the ester is comprised between of 1:1.1 to 1:16 inclusive.

In one embodiment, the weight ratio of the ester to the water is comprise between 3:1 to 0.33:1 inclusive.

In a preferred embodiment, the amount of perfume in the composition is ranging from 2% to 40% by weight, the amount of ester is ranging from 20% to 60% by weight and the amount of water is ranging from 15% to 75% by weight, relative to the total weight from the composition.

In a particular embodiment of the invention, the composition can preferably consists of water, a perfume and an ester comprising an ethoxylated glyceride derived from carboxylic acids having 6 to 22 carbon atoms moiety.

Alkane-1,2-Diol

The alcohol-free perfumed composition of the invention may optionally further comprise an alkane-1,2-diol, preferably having 3 to 10 carbon atoms, preferably 3 to 6 carbon atoms.

A preferred 1,2-alkanediol is pentylene glycol (INCI name) sold under the name HYDROLITE® 5 GREEN by Symrise.

Another preferred 1,2-alkanediol is caprylyl glycol (INCI name) sold under the name HYDROLITE® CG by Symrise.

Alkane diols such as glycols provide the cosmetic compositions with improved vaporizable properties by thinning said compositions.

The 1,2-alkanediol may be present in the composition in an amount ranging from 0.1% to 20% by weight, relative to the total weight of the composition.

Additional Ingredients

According to a particular embodiment of the invention, the alcohol-free perfumed composition may optionally further comprise one or more additional ingredients include for example colorants, pigments, conservatives and/or bactericides, providing some specific added benefits. Such additional ingredients are known compounds to a person skilled in the art. They can be synthetic or natural.

Method of Preparation of the Perfumed Compositions

The perfumed composition according to the present invention may be prepared, for example, by simple mixing all the ingredients; for example, by hand stirring or if need be using a mechanical mixer, the water and the ester of the present invention, mixing to form a clear and uniform solution, and finally adding the perfume to the solution and mixing to form a clear and uniform solution.

The so-called «fine perfume» is defined as the art of creating fragrances resulting from the combination of different essences, natural or artificial. The goal is to design a pleasant and unpleasant smell.

EXAMPLES

The examples which follow are used to illustrate the invention without however presenting a restrictive character. In these examples, the quantities of ingredients are given in weight percentage compared to the total weight of the composition.

Example 1

A series of ethanol-free perfumed compositions comprising:
60% of ester,
20% of perfume and
20% of water
have been prepared.

Fourteen solutions were prepared esters either according to the invention, comprising an ethoxylated glyceride derived from carboxylic acids having 6 to 22 carbon atoms moiety or presenting similar chemical structures while remaining outside of the scope the present invention.

| | INCI NAME | APPEARANCE |
|---|---|---|
| Composition 1 (Invention) | Glycereth-17 Cocoate | Transparent |
| Composition 2 (Invention) | Glycereth-20 Cocoate | Transparent |
| Composition 3 (Comparative) | Sorbeth-2 Hexaolenate | Non transparent (Milky) |
| Composition 4 (Comparative) | Sorbeth-2 Dilinoleate Crosspolymer | Non transparent (Semi-translucent) |
| Composition 5 (Comparative) | Glycereth-2 Cocoate | Non transparent (Cloudy) |
| Composition 6 (Comparative) | Glycereth-6 Tricocoate | Non transparent (Milky) |

-continued

| | INCI NAME | APPEARANCE |
|---|---|---|
| Composition 7 (Comparative) | Glycereth-7 Methoxides | Non transparent (Oil droplets) |
| Composition 8 (Comparative) | Glycereth-7 Glycolate | Non transparent (Oil droplets) |
| Composition 9 (Comparative) | Glycereth-7 Lactate | Non transparent (Oil droplets) |
| Composition 10 (Comparative) | Glycereth-7 Malate | Non transparent (Semi-translucent) |
| Composition 11 (Comparative) | Glycereth-7 Citrate | Non transparent (Semi-translucent) |
| Composition 12 (Comparative) | Glycereth-7 Triacetate | Non transparent (Cloudy) |
| Composition 13 (Comparative) | Glycereth-7 Capylate/Caprate | Non transparent (Cloudy) |
| Composition 14 (Comparative) | Glycereth-7 Cocoate | Non transparent (Cloudy) |

As can be seen from the results presented in the above table, the compositions of the invention comprising esters with an ethoxylated glyceride derived from carboxylic acids having 6 to 22 carbon atoms moiety provided clear and transparent solutions whereas comparative composition containing different esters resulted in non-transparent solutions.

Example 2

Two additional ethanol-free perfumed compositions (compositions 15 and 16) according to the invention having the following composition have been prepared:

| | Composition 2 | Composition 15 | Composition 16 |
|---|---|---|---|
| Ester (Glycereth-20 Cocoate) | 60% | 52% | 40% |
| Perfume | 20% | 26% | 10% |
| Water | 20% | 22% | 50% |

Compositions 2, 15 and 16 are all transparent.

In addition, the stability over time of these 3 compositions according to the invention was also evaluated by measuring the pH of the compositions after storage.

| | | Composition 2 | Composition 15 | Composition 16 |
|---|---|---|---|---|
| Initial | | 6.5 | 6.7 | 5.8 |
| 2 weeks | 5° C. | 6.5 | 6.3 | 5.7 |
| | 45° C. | 6.5 | 6.5 | 5.4 |
| 12 weeks | 5° C. | 6.4 | 6.5 | 5.5 |
| | 45° C. | 6.3 | 5.9 | 5.2 |

The pH of the compositions according to the invention remains stable over time during storage. The Variation of pH under the different storage conditions tested never exceeds 1 pH unit.

Example 3

Two additional ethanol-free perfumed compositions (compositions 17 and 18) according to the invention having the following composition have been prepared:

|  | Composition 17 | Composition 18 |
|---|---|---|
| Ester (Glycereth-20 Cocoate) | 24% | 24% |
| Perfume | 1.5% | 5% |
| Water | 74.5% | 74% |

Compositions 17 and 18 are both transparent.

Example 4

One additional ethanol-free perfumed composition (composition 19) according to the invention having the following composition has been prepared:

|  | Composition 19 |
|---|---|
| Ester (Glycereth-20 cocoate) | 25% |
| Perfume | 8% |
| Water | 57% |
| Pentylene glycol | 10% |

Composition 19 is transparent and shows improved vaporisable properties.

The invention claimed is:

1. An ethanol-free perfumed composition consisting essentially of water, a perfume, an ester comprising an ethoxylated glyceride derived from carboxylic acids having 6 to 22 carbon atoms moiety, and optionally one or more ingredients selected from the group consisting of an alkane-1,2-diol having 3 to 10 carbon atoms, colorants, pigments, conservatives and bactericides.

2. The composition according to claim 1, wherein the ethoxylated glyceride derived from carboxylic acids having 6 to 22 carbon atoms includes compounds of formula (I):

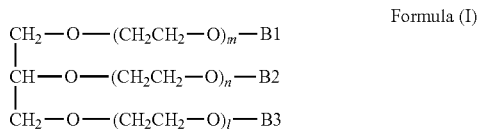

Formula (I)

wherein each of m, n, and l independently represent a number from 0 to 40, the sum of m, n and l being in the range of 8 to 200; and B1, B2, and B3 independently represent H or an acyl group having 6 to 22 carbon atoms, with the proviso that at least one of B1, B2 and B3 is an acyl group having 6 to 22 carbon atoms.

3. The composition according to claim 2, wherein the ethoxylated glyceride is a mixture of compounds of the above formula (I) comprising:
compounds of formula (I), wherein each of B1, B2 and B3 independently represent an acyl group having 6 to 22 carbon atoms;
(ii) compounds of formula (I), wherein two of B1, B2 and B3 independently represent an acyl group having 6 to 22 carbon atoms, the remainder representing H;
(iii) compounds of formula (I), wherein one of B1, B2 and B3 represents an acyl group having 6 to 22 carbon atoms; the remainder representing H;
(iv) compounds of formula (I), wherein each of B1, B2 and B3 represent H;
the weight ratio of the compounds (i)/(ii)/(iii) being 46 to 90/9 to 35/1 to 15.

4. The composition according to 2, wherein the acyl group having 6 to 22 carbon atoms is derived from a natural fat or oil or a synthetic glyceride.

5. The composition according to 13, wherein the acyl group having 6 to 22 carbon atoms is derived from a natural fat or oil or a synthetic glyceride.

6. The composition according to claim 1, wherein the weight ratio of the ester to the water is ranging from 3:1 to 0.33:1.

7. The composition according to claim 1, wherein the composition consists essentially of water, a perfume, an ester comprising an ethoxylated glyceride derived from carboxylic acids having 6 to 22 carbon atoms moiety, an alkane-1,2-diol having 3 to 10 carbon atoms and optionally one or more ingredients selected from the group consisting of colorants, pigments, conservatives and bactericides.

8. The composition according to claim 1, wherein the perfume is 1% to 40% by weight relative to the total weight of the composition.

9. The composition according to claim 1, wherein the weight ratio of perfume to ester is ranging from 1:1.1 to 1:16.

10. The composition according to claim 1, wherein the amount perfume is ranging from 2% to 40% by weight, the amount of ester is ranging from 20% to 60% by weight and the amount of water is ranging from 15% to 75% by weight, relative to the total weight of the composition.

11. The composition according to claim 1, wherein there is less than 5%4% by weight of ethanol in the composition.

12. The composition according to claim 1, wherein the composition consists of water, a perfume and an ester comprising an ethoxylated glyceride derived from carboxylic acids having 6 to 22 carbon atoms moiety.

13. A method for the preparation of an ethanol-free perfumed composition according to claim 1, comprising the following steps:
(a) preparing a solution of water and the ester under stirring, and mixing until a clear and uniform solution is obtained, and
(b) adding the perfume to the solution and mixing until a clear and uniform solution is obtained.

14. A method for the preparation of a fine perfume composition, a cosmetic composition or a personal cleansing composition, comprising adding the ethanol-free perfumed composition according to claim 1 to said fine perfume composition, said cosmetic composition or said personal cleansing composition.

15. A fine perfume composition, a cosmetic composition or a personal cleansing composition comprising the ethanol-free perfumed composition according to claim 1.

16. A method of improving solubility of a perfume in water and/or conferring transparency to a perfume composition consisting essentially of water and a perfume, comprising adding an ester comprising an ethoxylated glyceride derived from carboxylic acids having 6 to 22 carbon atoms moiety to a composition consisting essentially of water and a perfume.

* * * * *